United States Patent [19]

Setoyama et al.

[11] Patent Number: 5,157,179
[45] Date of Patent: Oct. 20, 1992

[54] METHOD FOR PRODUCING A CYCLOOLEFIN

[75] Inventors: Tohru Setoyama, Machida; Takahiko Takewaki, Yokohama; Takao Maki, Fujisawa, all of Japan

[73] Assignee: Mitsubishi Kasei Corporation, Tokyo, Japan

[21] Appl. No.: 726,199

[22] Filed: Jul. 5, 1991

[30] Foreign Application Priority Data

Jul. 13, 1990 [JP] Japan ................................ 2-185842

[51] Int. Cl.$^5$ ................................................ C07C 5/10
[52] U.S. Cl. ...................... 585/266; 585/269; 585/271; 585/273; 585/500
[58] Field of Search ............... 585/266, 269, 271, 273, 585/500

[56] References Cited

U.S. PATENT DOCUMENTS

| | | | |
|---|---|---|---|
| 3,637,878 | 1/1972 | Hansford | 585/269 |
| 3,703,461 | 11/1972 | Hansford | 585/269 |
| 4,734,536 | 3/1988 | Nagahara et al. | 585/273 |

Primary Examiner—Patrick P. Garvin
Assistant Examiner—E. D. Irzinski
Attorney, Agent, or Firm—Oblon, Spivak, McClelland, Maier & Neustadt

[57] ABSTRACT

A method for producing a cycloolefin which comprises partially hydrogenating an aromatic hydrocarbon with hydrogen in a liquid phase in the presence of water and a catalyst having as main component ruthenium supported on a carrier, to form the corresponding cycloolefin, wherein an oxide with the total pore volume of pores having radii of from 20 to 100,000 Å being from 0.3 to 10 cc/g and with the volume of pores having radii of from 20 to 200 Å constituting at most 15% of the total pore volume, is used as the carrier for the catalyst.

15 Claims, No Drawings

METHOD FOR PRODUCING A CYCLOOLEFIN

The present invention relates to a method for producing a cycloolefin which comprises partially hydrogenating aromatic hydrocarbons to form the corresponding cycloolefins, particularly cyclohexene.

Cycloolefins are important intermediate compounds for lactams, dicarboxylic acids as starting materials for polyamides, lysines, medicines and agricultural chemicals.

Heretofore, a number of methods have been known with respect to methods for the production of cycloolefins, such as partial hydrogenation of aromatic hydrocarbons, dehydration of cycloalkanols and dehydrogenation and oxidative dehydrogenation of cycloalkanes. In all the above methods, aromatic hydrocarbons are used as the starting material. Thus, if a cycloolefin can be produced efficiently by partially hydrogenating an aromatic hydrocarbon, the reaction process can be the most simplified, such being desirable from viewpoint of the industrial process.

As a method for producing a cycloolefin by partially hydrogenating an aromatic hydrocarbon, the following methods have been known:

1) Partial hydrogenation in the presence of water and a catalyst comprising an alkali agent and at least one reduced cation of Group VIII elements in the Periodic Table (Japanese Examined Patent Publication No. 22850/1981).

2) Partial hydrogenation in the presence of water and a ruthenium-silica catalyst obtained by hydrolyzing a solution mixture of ruthenium glycoxide and ethyl silicate, followed by reduction with hydrogen at 400° C. (Japanese Unexamined Patent Publication No. 155328/1984).

3) Partial hydrogenation in the presence of a catalyst having ruthenium mainly supported on a metal oxide such as silica or alumina, water and cobalt sulfate (Japanese Unexamined Patent Publication No. 130926/1982).

4) Partial hydrogenation in an acidic aqueous solution in the presence of a ruthenium catalyst and a cation selected from Group IA and IIA metals in the Periodic Table and manganese (Japanese Examined Patent Publication No. 7607/1982).

5) Partial hydrogenation in the presence of a catalyst having ruthenium supported on a barium sulfate carrier, water and a sulfate selected from sulfates of Li, Co, Fe and Zn (Japanese Unexamined Patent Publication No. 40226/1986).

6) Partial hydrogenation in the presence of a micro particle of ruthenium metal having an average size of at most 200 Å, water and a zinc compound (Japanese Unexamined Patent Publication No. 50930/1986, Japanese Unexamined Patent Publication No. 45544/1987).

However, these methods have some problems respectively and are not necessarily useful from the industrial viewpoint.

Namely, 1) has problems such as separation of the reaction product and corrosion by chlorine ions in addition to the extremely complicated reaction system.

2) has such problems that cost for producing a catalyst is high and the yield and selectivity are not so high, although the reaction system is simplified.

3) and 4) have a problem that the yield and selectivity do not reach the satisfactory level.

5) provides a relative high level of yield and selectivity, but they are still unsatisfactory.

6) provides a high yield and selectivity, but has the following problems:

a) High temperature and pressure are required in preparation of a catalyst, b) The activity per ruthenium is extremely small, and c) Adhesion of ruthenium on the reactor wall takes place, whereby some special technique is required in the catalyst system.

It is an object of the present invention to overcome the above-mentioned problems and to provide a method for producing a cycloolefin useful from the industrial viewpoint. The present inventors have conducted extensive research to attain the above object, and as a result, have found that a selectivity or a formation rate is influenced by surface properties and a pore volume of a carrier for catalyst. The present invention has been accomplished on the basis of this discovery.

The present invention provides a method for producing a cycloolefin which comprises partially hydrogenating an aromatic hydrocarbon with hydrogen in a liquid phase in the presence of water and a catalyst having as main component ruthenium supported on a carrier, to form the corresponding cycloolefin, wherein an oxide with the total pore volume of pores having radii of from 20 to 100,000 Å being from 0.3 to 10 cc/g and with the volume of pores having radii of from 20 to 200 Å constituting at most 15% of the total pore volume, is used as the carrier for the catalyst.

Now, the present invention will be described in detail with reference to the preferred embodiments.

The aromatic hydrocarbon used in the method of the present invention may be benzene, toluene, xylene or benzene substituted by a lower alkyl group. It is not necessary to use an aromatic hydrocarbon having an especially high purity, and may contain a cycloparaffin or a lower paraffin hydrocarbon.

The carrier for the catalyst used in the method of the present invention may be a carrier commonly used such as $SiO_2$, $Al_2O_3$, $ZrO_2$, $TiO_2$ or $MgO$, preferably $SiO_2$, $Al_2O_3$, $ZrO_2$, a mixture thereof or a compound oxide such as $ZrSiO_4$. The carrier must meet the following specific requirements in the amount of the fine pore structure and the proportion thereof:

Namely, as measured by the method of mercury penetration, the carrier for the catalyst used in the present invention has such pore distribution and pore volume that the total volume of pores having radii of from 20 to 10,000 Å is from 0.3 to 10 cc/g, preferably from 0.3 to 5 cc/g, more preferably from 0.3 to 3 cc/g, and the volume of pores having radii from 20 to 200 Å constitutes at most 15%, preferably at most 10% of the total pore volume (in other words, the volume of pores having radii of from 200 to 100,000 Å constitutes at least 85%, preferably at least 90% of the total pore volume). Further, the pore volume of pores having radii of from 20 to 200 Å is, as the absolute value, preferably at most 0.2 cc/g, more preferably at most 0.15 cc/g.

The carrier having such properties can be obtained by subjecting, for example, $SiO_2$ or $Al_2O_3$ prepared by the alkoxide method or commercially available α-alumina or $ZrSiO_4$ (zircon), having a relatively large pore size to heat treatment at a high temperature, preferably at least 600° C., more preferably at least 800° C. However, the preparation of the carrier is by no means restricted by such a specific method.

Although it is not clear that such a carrier having the above-mentioned pore structure is particularly effective to partial hydrogenation, it is considered as follows:

1) Such a carrier does not substantially have a fine pore structure, whereby a cycloolefin produced is not susceptive to a successive hydrogenation to a cycloparaffin which is considered to be formed by a readsorption of the cycloolefin.

2) By using such a carrier, ruthenium species which are particularly effective for partial hydrogenation can be produced in the preparation of the catalyst.

Ruthenium which is the active component of the catalyst can be used alone or in combination with other metal components supported on the carrier. In the latter case, the metal component used in addition to ruthenium may be manganese, iron, cobalt, zinc, nickel, gold, silver or copper and so on. By incorporation of such a metal component, a selectivity for the desired product can be increased although the reaction rate is more or less decreased as compared with the case using ruthenium alone, such being advantageous from the industrial viewpoint.

The catalyst is prepared in accordance with conventional methods usually used for the preparation of catalysts supported on carriers. Namely, the evaporation to dryness method wherein a carrier is immersed in a solution containing an active component for a catalyst and the active component is fixed by evaporating a solvent under stirring, the spray method wherein a solution containing an active component for a catalyst is sprayed while maintaining a carrier in a dry condition or a supporting method by immersion wherein a carrier is immersed in a solution containing an active component for a catalyst and then subjected to filtration, etc., may be suitably be employed.

The starting ruthenium compound to be used for the preparation of the catalyst which is the main active component for the catalyst may be a halide, nitrate, hydroxide or oxide of ruthenium, ruthenium carbonyl, a complex compound such as ruthenium amine complex or ruthenium alkoxide.

Other metal compound such as Manganese, iron, cobalt, zinc, gold silver or copper to be used for the preparation of the catalyst as the component in addition to ruthenium may be a halide, nitrate, acetate or sulfate of each metal. Further, these metal components can be supported on the carrier at the same time when the ruthenium compound is supported, or ruthenium is preliminarily supported and then the other metal component is supported, or the other metal component is preliminarily supported and then ruthenium is supported. Either cases can be employed.

A solvent for an active component to be used in the preparation of the catalyst, may be water, an alcohol, acetone or tetrahydrofuran.

In the catalyst prepared in accordance with the above-mentioned method, ruthenium is activated by reduction before using. As the reducing agent, well known reducing agents such as hydrogen, carbon monoxide, alcohol vapour, hydrazine, formalin and sodium borohydride may be used. Hydrogen is particularly preferred. In this case, the reduction is usually conducted at a temperature from 100° to 500° C., preferably from 120° to 450° C. If the reduction temperature is not more than 100° C., the reducing rate of ruthenium decreases. On the other hand, the reduction temperature is not less than 500° C., agglomeration of ruthenium takes place, whereby the yields and selectivity of cycloolefin produced will decrease.

The amount of ruthenium supported on the carrier is usually in a range of from 0.001 to 10% by weight, preferably from 0.05 to 5% by weight to the support.

In the case wherein a metal component such as manganese, iron, cobalt or zinc is used in addition to ruthenium, the atomic ratio of the metal to ruthenium is usually within a range of from 0.01 to 20, preferably from 0.1 to 10.

According to the present invention, water is added to the reaction system. The amount of water to the aromatic hydrocarbon is usually from 0.01 to 10, preferably from 0.1 to 5 times by volume.

According to the present invention, a specific metal salt may be added to the reaction system. By the addition of the metal salt, the selectivity of a cycloolefin formed can be considerably improved although the formation rate of the cycloolefin is suppressed. However, in a case wherein the pH tends extremely to an acidic condition, a reactor made of a material such as titanium or zircon is preferably used.

As the metal salt to be used in the method of the present application, a salt of Group IA elements and Group IIA elements of the Periodic Table or a metal such as Mn, Fe, Co or Zn is effective. Particularly, a preferable result can be obtained by addition of a salt of zinc. As the salt of each metal, a weak acid salt such as carbonate or acetate and a strong acid salt such as chloride, sulfate or nitrate may be used. The weight ratio of the metal salt to water present in the reaction system is usually in a range of from $1 \times 10^{-5}$ to 1, preferably from $1 \times 10^{-4}$ to 0.1.

Further, the pressure of hydrogen during the reaction is usually within a range of from 0.1 to 20 MPa, preferably from 0.5 to 10 MPa. If the pressure is not less than 20 MPa, it is not effective from the industrial viewpoint. On the other hand, if the pressure is not more than 0.1 MPa, the reaction rate decreases remarkably.

The reaction temperature is usually within a range of from 50° to 250° C., preferably from 100° to 220° C. The selectivity of a cycloolefin formed will decrease at a reaction temperature of not less than 250° C. while the reaction rate will considerably decrease at a reaction temperature of not more than 50° C., such being undesirable.

The reaction system of the method according to the present invention is a reaction in a liquid phase, and is conducted by a batch process using at least one reaction vessel or by a continuous process. There is no particular restriction as to the reaction system.

Now, the method of the present invention will be described in further detail with reference to the Examples. However, it should be understood that the present invention is by no means restricted by such specific Examples.

The conversion and the selectivity used in the Examples and Comparative Examples are defined by the following equations:

$$\text{Conversion (\%)} = \frac{\text{Number of mols of an aromatic hydrocarbon consumed in the reaction}}{\text{Number of mols of an aromatic hydrocarbon supplied to the reaction}} \times 100$$

Selectivity (%) =

-continued $$\frac{\text{Number of mols of a cycloolefin formed by the reaction}}{\text{Number of mols of an aromatic hydrocarbon consumed in the reaction}} \times 100$$

Further, in the following Examples and Comparative Examples, the reaction time was controlled so that the conversion of the starting material aromatic hydrocarbon became about 20%.

EXAMPLE 1

Preparation of carrier

To a mixture of 60 g of ethyl orthosilicate, 50 g of desalted water and 125 ml of ethanol, 60 cc of a 28% aqueous ammonia was added under stirring to hydrolyze ethyl orthosilicate. After digestion of the precipitate thus formed, it was subjected to filtration and washed with desalted water. The precipitate was dried under vacuum at 80° C. by a rotary evaporator.

The silica gel thus obtained was charged in a silica glass reaction tube and subjected to heat treatment under an air stream at 1,000° C. for 4 hours. After cooling to room temperature, $SiO_2$ thus obtained was used as a carrier.

The pore distribution and the pore volume of the carrier thus obtained were measured by the mercury penetration method.

Preparation of catalyst

In a ruthenium chloride aqueous solution containing ruthenium in a pre-determined amount, $SiO_2$ prepared in the above step was immersed at 60° C. for 1 hour, and water was removed by a rotary evaporator. 2.0 g of 0.5 wt % $Ru/SiO_2$ thus obtained was charged in a Pylex reaction tube and reduced in a hydrogen stream at 200° C. for 3 hours to activate the catalyst.

Reaction

Into a stainless steel autoclave having an internal volume of 500 ml which was preliminarily thoroughly purged with nitrogen, 2.0 g of the above catalyst and 80 ml of benzene were sequentially introduced.

Hydrogen gas was further introduced and the reaction was conducted under stirring (1,200 r.p.m.) for 5 minutes under a pressure of 5.0 MPa at a temperature of 180° C. After completion of the reaction, the autoclave was cooled and an oil phase was sampled to analyze the products by gas chromatography. The results thus obtained are shown in Table 1.

EXAMPLE 2

The operation was conducted in the same manner as in Example 1 except that 2.0 g of 0.2 wt % $Ru/SiO_2$ was used as catalyst. The results thus obtained are shown in Table 1.

COMPARATIVE EXAMPLE 1

The operation was conducted in the same manner as in Example 1 except that SIO-4 which is a reference carrier for catalyst stipulated in the Catalyst Association was subjected to heat treatment at 1,000° C. for 4 hours was used as a carrier. The results thus obtained are shown in Table 1.

EXAMPLE 3

Preparation of catalyst

Into an aqueous solution containing ruthenium chloride and manganese chloride at pre-determined amounts, $SiO_2$ prepared in Example 1 was immersed at 60° C. for 1 hour, and water was removed by a rotary evaporator. Ru/Mn (0.5-0.5wt %)/$SiO_2$ thus obtained was charged in a Pylex reaction tube and reduced in a hydrogen stream at 200° C. for 3 hours to activate the catalyst.

Reaction

Into a stainless steel autoclave having an internal volume of 500 ml was preliminarily thoroughly flushed with nitrogen and 14.4 g of zinc sulfate heptahydrates ($ZnSO_4 \cdot 7H_2O$), 2.0 g of the above catalyst and 80 ml of benzene were sequentially added.

Hydrogen gas was further introduced and the reaction was conducted under stirring (1,200 r.p.m.) under a pressure of 5.0 MPa at a temperature of 180° C. The result thus obtained are shown in Table 1.

EXAMPLE 4

A carrier was prepared in the same manner as in Example 1 except that the heat treatment temperature was changed from 1,000° C. to 600° C. By using the carrier, a catalyst was prepared and a reaction was conducted in the same manner as in Example 3. The results thus obtained are shown in Table 1.

COMPARATIVE EXAMPLE 2

The operation was conducted in the same manner as in Example 3 except that the carrier in Comparative Example 1 was used. The results thus obtained are shown in Table 1.

COMPARATIVE EXAMPLE 3

To an aqueous solution containing ruthenium chloride and zinc chloride at pre-determined amounts, a 30% NaOH aqueous solution was added under stirring at a high speed and the solution was further stirred at 80° C. for 3 hours. The solution was cooled to room temperature, whereby a 5% NaOH aqueous solution containing black precipitate was obtained. This solution was charged in an autoclave and reduced with hydrogen under a pressure of 50 kg/G at a temperature of 150° C. for 10 hours. After cooling, the reaction solution was subjected to filtration and a black precipitate thus obtained was dried in argon atmosphere, whereby a ruthenium fine particle (average particle size: 55 Å) catalyst containing 7% of zinc.

The operation was conducted in the same manner as in Example 3 except that 0.4 g of the catalyst thus obtained was used. The results thus obtained are shown in Table 1.

It is clear from Table 1 that a ruthenium catalyst which is not supported on a carrier has extremely small activity per ruthenium.

EXAMPLE 5

The operation was conducted in the same manner as in Example 3 except that $SiO_2-ZrO_2$ (molar ratio 1:1) which was obtained by thoroughly mixing commercially available $SiO_2$ (purity: at least 99.99%, calcined at 600° C.) and $ZrO_2$ (purity: at least 99.99%, calcined at 600° C.) and then subjecting to further heat treatment at 1,100° C., was used as a carrier. The results thus obtained are shown in Table 1.

EXAMPLE 6

The operation was conducted in the same manner as in Example 3 except that a carrier prepared by subjecting a commercially available zirconium silicate ($ZrSiO_4$, content: 97.33%, manufactured by Mitsuwa Kagaku K.K.) to heat treatment at 900° C. was used. The results thus obtained are shown in Tables 1 and 2.

COMPARATIVE EXAMPLE 4

To a solution mixture of partial condensate of ethyl orthosilicate and water, and zirconium butoxide, water and aqueous ammonia were sequentially added for gellation. Water was removed from the gel by a rotary evaporator to obtain a white solid. The white solid was subjected to heat treatment in a muffle furnace in air atmosphere at 600° C. $SiO_2$-$ZrO_2$ (molar ratio 1:1) thus obtained was used as the carrier. The operation was conducted in the same manner as in Example 3 except that the carrier prepared above was used. The results thus obtained are shown in Table 1.

EXAMPLE 7

The operation was conducted in the same manner as in Example 3 except that commercially available α-alumina subjected to heat treatment at 1,000° C. for 4 hours was used as the carrier. The result thus obtained are shown in Table 1.

COMPARATIVE EXAMPLE 5

The operation was conducted in the same manner as in Example 3 except that ALO-2 which is a reference carrier for catalyst stipulated by the Catalyst Association, was used as the carrier. The results thus obtained are shown in Table 1. As compared with Example 7, the selectivity of the cyclohexene is low, such being inappropriate as industrial method.

EXAMPLES 8-12

A case wherein manganese chloride was not added in the preparation of catalyst of Example 6 was given as Example 8 and cases wherein zinc chloride, chloroauric acid, cobalt chloride and iron chloride were used, respectively, instead of manganese chloride were given as Examples 9-12, respectively. The results are shown in Table 2.

It is clear from Table 2 that these metal salts are effective to improve the selectivity of a cyclohexene.

TABLE 2

| Examples | Composition of catalyst | Bz conversion (%) | CHE selectivity (%) | CHE formation rate |
|---|---|---|---|---|
| 8 | Ru(0.5 wt %)/SiZrO$_4$ | 20.4 | 75.3 | 69.3 |
| 9 | Ru-Zn(0.5–0.5 wt %) SiZrO$_4$ | 19.9 | 81.5 | 35.1 |
| 10 | Ru-Au(0.5–2.0 wt %) SiZrO$_4$ | 20.0 | 85.7 | 30.9 |
| 11 | Ru-Fe(0.5–0.5 wt %) SiZrO$_4$ | 20.0 | 78.7 | 40.6 |
| 12 | Ru-Co(0.5–0.5 wt %) SiZrO$_4$ | 19.9 | 78.0 | 56.0 |
| 6 | Ru-Mn(0.5–0.5 wt %)/ SiZrO$_4$ | 20.5 | 82.5 | 43.6 |

Bz: benzene, CHE: cyclohexane, CHE formation rate: mol-cyclohexene/g.Ru-hour

EXAMPLES 13-14

The operation was conducted in the same manner as in Example 6 except that instead of 14.4 g of $ZnSO_4.7H_2O$, the same amount of $CoSO_4.7H_2O$ or $Li_2SO_4.H_2O$ was used. The results thus obtained are shown in Table 3.

TABLE 3

| Examples | Salt added | Reaction time (minute) | Conversion (%) | Selectivity (%) | CHE formation rate |
|---|---|---|---|---|---|
| 13 | CoSo$_4$.7H$_2$O | 12 | 21.3 | 77.6 | 74.6 |
| 14 | Li$_2$SO$_4$.H$_2$O | 83 | 20.4 | 78.3 | 10.4 |

Bz: benzene, CHE: cyclohexane, CHE formation rate: mol-cyclohexene/g.Ru-hour

According to the present invention, a cycloolefin can be obtained with a high selectivity or a high formation rate as compared with a conventional method using a carrier with a usual fine pore structure. Thus, the method of the present invention is useful from the industrial viewpoint.

We claim:

1. A method for producing a cycloolefin which comprises partially hydrogenating an aromatic hydrocarbon with hydrogen in a liquid phase in the presence of water and a catalyst having as main component ruthenium supported on a carrier, to form the corresponding cycloolefin, wherein an oxide with the total pore volume

TABLE 1

| | Composition of catalyst | Total pore volume (cc/g) | Fine pore volume (cc/g) | (B/A) × 100 (%) | Reaction time (minute) | Bz conversion (%) | CHE selectivity (%) | CHE formation rate |
|---|---|---|---|---|---|---|---|---|
| Example 1 | Ru(0.5 wt %)/SiO$_2$ | 1.495 | 0.088 | 5.9 | 5.0 | 21.1 | 39.2 | 89.6 |
| Example 2 | Ru(0.2 wt %)/SiO$_2$ | 1.495 | 0.088 | 5.9 | 5.5 | 21.8 | 30.5 | 163.7 |
| Comparative Example 1 | Ru(0.5 wt %)/SIO-4 | 0.706 | 0.409 | 57.9 | 3.1 | 25.2 | 5.7 | 25.1 |
| Example 3 | Ru-Mn(0.5–0.5 wt %)/SiO$_2$ | 1.495 | 0.088 | 5.9 | 71 | 21.0 | 87.9 | 14.1 |
| Example 4 | Ru-Mn(0.5–0.5 wt %)/SiO$_2$ | 1.767 | 0.099 | 5.6 | 89 | 19.8 | 82.0 | 9.9 |
| Comparative Example 2 | Ru-Mn(0.5–0.5 wt %)/ SIO-4 | 0.706 | 0.409 | 57.9 | 22 | 17.4 | 56.7 | 24.3 |
| Comparative Example 3 | Ru fine particle (ZnO.7 wt %) | — | — | — | 15 | 21.8 | 83.3 | 1.6 |
| Example 5 | Ru-Mn(0.5– 0.5 wt %)/SiZrO$_4$ | 0.502 | 0.046 | 9.2 | 21 | 23.2 | 82.3 | 49.2 |
| Example 6 | Ru-Mn(0.5– 0.5 wt %)/SiZrO$_4$ | 0.343 | 0.017 | 5.0 | 21 | 20.5 | 82.5 | 43.6 |
| Comparative Example 4 | Ru-Mn(0.5– 0.5 wt %)/SiZrO-4 | 0.332 | 0.213 | 64.2 | 68 | 19.3 | 64.7 | 11.3 |
| Example 7 | Ru-Mn(0.5–0.5 wt %)/ α-alumina | 0.674 | 0.028 | 4.2 | 70 | 21.2 | 75.2 | 12.3 |
| Comparative Example 5 | Ru-Mn(0.5–0.5 wt %)/ ALO-2 | 1.447 | 0.592 | 40.9 | 19 | 18.6 | 50.8 | 26.9 |

Total pore volume A: Total pore volume of pores having radii of from 20 to 100,000 Å
Fine pore volume B: Pore volume of pores having radii of from 20 to 200 Å
Bz: benzene, CHE: cyclohexene, CHE formation rate: mol-cyclohexene/g.Ru-hour of pores having radii of from 20 to 100,000 Å being from 0.3 to 10 cc/g and with the volume of pores having radii of from 20 to 200 Å constituting at most 15% of the total pore volume, is used as the carrier for the catalyst.

2. A method for producing a cycloolefin which comprises partially hydrogenating an aromatic hydrocarbon with hydrogen in a liquid phase in the presence of water, a metal salt and a catalyst having as main component ruthenium supported on a carrier, to form the corresponding cycloolefin, wherein an oxide with the total pore volume of pores having radii of from 20 to 100,000 Å being from 0.3 to 10 cc/g and with the volume of pores having radii of from 20 to 200 Å constituting at most 15 % of the total pore volume, is used as the carrier for the catalyst.

3. The method according to claim 1 or 2, wherein the pore volume of pores having radii of from 20 to 200 Å is at most 0.2 cc/g.

4. The method according to claim 1 or 2, wherein the total pore volume of pores having radii of from 20 to 100,000 Å is from 0.3 to 5 cc/g.

5. The method according to claim 1 or 2, wherein the volume of pores having radii of from 20 to 200 Å constitutes at most 10% of the total pore volume.

6. The method according to claim 1 or 2, wherein the carrier is $SiO_2$.

7. The method according to claim 1 or 2, wherein the carrier is $ZrSiO_4$.

8. The method according to claim 1 or 2, wherein the concentration of ruthenium supported on the carrier is from 0.001 to 10% by weight.

9. The method according to claim 1 or 2, wherein in addition to ruthenium at least one metal other than ruthenium is supported on the carrier.

10. The method according to claim 9, wherein the metal is at least one member selected from the group consisting of manganese, cobalt and zinc.

11. The method according to claim 10, wherein the atomic ratio of the metal to ruthenium supported on the carrier is from 0.01 to 20.

12. The method according to claim 1 or 2, wherein the aromatic hydrocarbon is benzene.

13. The method according to claim 1 or 2, wherein the volume ratio of the water to the aromatic hydrocarbon is from 0.01 to 10.

14. The method according to claim 2, wherein the metal salt is a salt of zinc.

15. The method according to claim 2, wherein the weight ratio of the metal salt to the water is from $1 \times 10^{-5}$ to 1.

* * * * *